United States Patent [19]

Okamoto et al.

[11] Patent Number: 5,345,330
[45] Date of Patent: Sep. 6, 1994

[54] SINGLE CRYSTAL OF 3-(2-FURYL)METHACRYLIC ACID ANHYDRIDE

[75] Inventors: Hidenori Okamoto; Norihiro Tanaka, both of Tsukuba; Keisuke Sasaki, Tokyo, all of Japan

[73] Assignee: Tokuyama Corporation, Tokuyama, Japan

[21] Appl. No.: 929,413

[22] Filed: Aug. 14, 1992

[30] Foreign Application Priority Data

Apr. 20, 1992 [JP] Japan .................. 4-099531

[51] Int. Cl.$^5$ .............................. H03F 7/00
[52] U.S. Cl. .................................. 359/326
[58] Field of Search ............. 372/39, 41, 21; 252/301.17; 359/326, 328

[56] References Cited

U.S. PATENT DOCUMENTS 5,070,505 12/1991 Dixon .................. 372/22
5,101,411 3/1992 Terao et al. ............ 372/21

FOREIGN PATENT DOCUMENTS 0335641 10/1989 European Pat. Off. .
420216A2 3/1991 European Pat. Off. .
435138A1 3/1991 European Pat. Off. .
0420216 4/1991 European Pat. Off. .
0435138 7/1991 European Pat. Off. .

OTHER PUBLICATIONS

WO90/01724, Jean-Francois Fauvarque et al, "Organic Material For Non-Linear Optics", Feb. 2, 1990.
European Search Report, 92307447.0, Tokuyama Soda Kabushiki Kaisha, Dec. 7, 1993.
Patent Abstracts of Japan, JP3126926, Teijin Ltd., Aug. 29, 1991 "Second Harmonic Wave Generating Material for Nonlinear Optics".
Patent Abstracts of Japan, JP1213333, Idemitsu Kosan Co. Ltd. Nov. 21, 1989 "Novel Polymer and Organic . . . Material Composed Thereof".
Patent Abstracts of Japan, JP2134623, Teijin Ltd., Aug. 8, 1990, "Nonlinear Optical Material Consisting of Amine Salt . . . Organic Compound".
Chemical Abstracts, vol. 102, No. 23, Jun. 10, 1985, 203867k, V. F. Pozdnev, 3-(2-Furyl)acrylic Anhydride.
Chemical Abstracts, vol. 105, No. 11, Sep. 15, 1986, 97923a, V. F.Pozdnev, Synthesis of N–furylacryloyl Derivatives . . . Anhydride.
Chemical Abstracts, vol. 89, No. 19, Nov. 6, 1978, 163320f, J. Kovac et al, Furan Derivatives . . . 3-(-2-furyl)acrylic Acid.

*Primary Examiner*—James W. Davie
*Attorney, Agent, or Firm*—Sherman and Shalloway

[57] ABSTRACT

A single crystal of 3-(2-furyl)methacrylic acid anhydride,
(a) which has an absorption edge in a region off light having a wavelength of not more than 450 nm
(b) which exhibits non-linear optical activity,
(c) which has a single crystal structure having a size of which the largest side is at least 1 mm long, and
(d) which consists of 3-(2-furyl)methacrylic acid anhydride off the following formula (I).

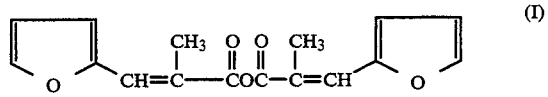

This single crystal of FMA is useful as a material for manufacturing a light wavelength conversion element, an optical switch element or the like.

7 Claims, No Drawings

SINGLE CRYSTAL OF 3-(2-FURYL)METHACRYLIC ACID ANHYDRIDE

DETAILED DESCRIPTION OF THE INVENTION

The present invention relates to a single crystal of 3-(2-furyl)methacrylic acid anhydride, and a light wavelength conversion element and an optical switch element in which the above crystal is used.

Non-linear optical materials have effects of converting a light wavelength and modulating light intensity when irradiated with light such as laser light, and attract attention as essential materials in the fields of optoelectronics such as optical recording, data processing and optical communication. Studies and developments of non-linear optical materials are therefore vigorously under way.

Inorganic crystals of potassium dihydrogenphosphate (KDP) and lithium niobate (LN) are well known as non-linear optical materials, and these inorganic crystals are being practically used in a light wavelength conversion element, an optical shutter and an optical modulator for laser light. However, these inorganic crystals are poor in operability, and rather insufficient in non-linear optical effects. On the other hand, it is known that some organic compounds such as urea and 2-methyl-4-nitroaniline (MNA) have high non-linear optical effects. However, the non-linear optical effects of these organic compounds are not fully satisfactory, either. Further, since these single crystal compounds having relatively high non-linear optical effects show generally their own colors to a considerable degree and absorb light in short visible wavelength region, these single crystal compounds are restricted in their usable wavelength region. In actual case for frequency doubling (light having a ½ wavelength) of semiconductor laser light having a wavelength in the region of 800 nm, the absorption is resulted in a decrease of doubled wave output. It is therefore under way to develop materials having high non-linear optical activity and having an absorption edge on a short wavelength side.

EP 0 420 216 A2 discloses a non-linear optical material consisting essentially of 3-(2-thienyl)-1-(4-methylphenyl)propene-3-one represented by the following formula:

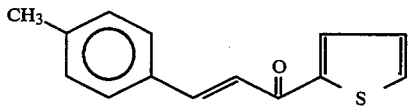

EP 0 435 138 A1 discloses a non-linear optical material comprising a benzalacetofuron derivative represented by the following formula:

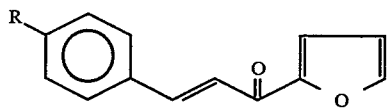

wherein R is $CH_3$, $CH_3S$, Br, CN or $NO_2$.

It is an object of the present invention to provide a single crystal of 3-(2-furyl)methacrylic acid anhydride.

It is another object of the present invention to provide a single crystal of 3-(2-furyl)methacrylic acid anhydride having high non-linear optical effects and having an absorption edge on a short wavelength side.

It is further another object of the present invention to provide a single crystal of 3-(2furyl)methacrylic acid anhydride having a size of which the largest side is at least 1 mm long.

It is still further another object of the present invention to provide a light wavelength conversion element formed from the single crystal of the present invention.

It is yet another object of the present invention to provide an optical switch element formed from the single crystal of the present invention.

Still further another objects and advantages of the present invention will be apparent from the following description.

According to the present invention, the above objects and advantages of the present invention are achieved, first, by a single crystal of 3-(2-furyl)methacrylic acid anhydride, (a) which has an absorption edge in a region of light having a wavelength of not more than 450 nm
(b) which exhibits non-linear optical activity,
(c) which has a single crystal structure having a size of which the largest side is at least 1 mm long, and
(d) which consists of 3-(2-furyl)methacrylic acid anhydride (to be sometimes referred to as FMA hereinafter) of the following formula (I).

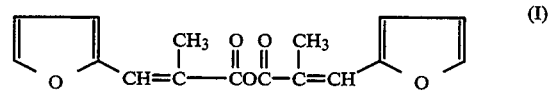

The term "single crystal" in the present invention refers to a crystalline solid having a crystallographic axis which is in one direction in any portion of the solid. However, the crystalline solid may have a slight disorder or slight lattice defect partially.

The FMA provided by the present invention is a novel compound. It can be confirmed by means of, for example, infrared absorption spectrum, $^1$H-nuclear magnetic resonance spectrum, mass spectrum and elemental analysis that said compound is the compound of the formula (I). That is, the infrared absorption spectrum of the above compound shows absorption based on the C=O group of acid anhydride at 1,750 cm$^{-1}$ and absorption based on the C=C bonds at 1,622 cm$^{-1}$. The $^1$H-nuclear magnetic resonance spectrum shows the number of hydrogen atoms and bonding modes. In the mass spectrum, there are observed a molecular ion peak (M$^+$) at m/e=286 and a peak corresponding to M$^{2+}$/2−0 at 135. Further, weight percents of carbon and hydrogen are determined on the basis of the elemental analysis, and the weight percentage of oxygen can be calculated by deducting the total of weight percents of the carbon and hydrogen from 100. Thus, the composition formula of the above compound can be determined.

FMA of the present invention is a transparent, colorless crystalline solid. This compound is soluble in ordinary organic solvents such as benzene, acetone, chloroform and ether.

Further, it can be confirmed, for example, through a polarization microscope that FMA of the present invention is a single crystal. That is, when FMA crystal is observed under a cross Nicol system, it shows a uniform high contrast view due to light extinction, which confirms that FMA crystal is a single crystal. Also, being a single crystal can be confirmed by X-ray crystal analysis.

Further, the FMA single crystal of the present invention is a mechanically hard single crystal having a Vickers hardness of at least 20. And, the FMA single crystal of the present invention is so stable at room temperature and so easily processable by cutting and polishing that it is suitable for a material in forming an element and a device.

The FMA single crystal of the present invention is generally obtained in the form of a prism or a pyramid. The FMA single crystal has a size of which the largest side is at least 1 mm long and the smallest side is generally at least 0.5 mm long. The FMA single crystal generally preferably has the form of a prism or a pyramid having a size of which the largest side is at least 1 mm long, preferably at least 2 mm long and the smallest side is at least 0.5 mm long, preferably at least 1 mm long.

The FMA single crystal of the present invention can be produced by any method known per se. According to a typical method generally preferably employed, for example, a colorless, fine-powder single crystal of FMA can be obtained by stirring under heating 3-(2-furyl)methacrylic acid in the presence of a dehydrating agent. The dehydrating agent is preferably selected from acid anhydrides such as acetic acid anhydride, acid chlorides such as acetyl chloride, and chlorides such as thionyl chloride, oxalyl chloride, chloroethyl carbonate and phosphoryl chloride.

The above dehydration is generally carried out in the absence of a solvent, but it is preferably carried out in the presence of a solvent. The solvent is selected from benzene, toluene, chloroform, ether and acetonitrile. The reaction temperature is between 0° C. and 150° C., preferably between 20° C. and 100° C. Depending upon reaction temperatures, the reaction time is from several minutes to several days.

When hydrogen chloride is formed as a by-product in the above reaction, generally, it is preferred to use a hydrogen chloride scavenger. The scavenger can be selected from known scavengers such as triethylamine, pyridine, sodium carbonate, potassium carbonate and sodium hydrogencarbonate.

To obtain a single crystal having the desired large size, the above fine-powder single crystal is then subjected to, for example, a melting method in which the fine-powder single crystal is melted under heat and then cooled; a solvent evaporation method in which it is dissolved in a solvent such as acetone, ethanol, chloroform, tetrahydrofuran, ethyl acetate or benzene and then the solvent is removed; a temperature gradient method in which the temperature is decreased; a vacuum deposition method; or an epitaxial growth method.

In the above manner, the single crystal of the present invention can be obtained as a single crystal having a size of which the largest side is at least 1 mm long, preferably at least 2 mm long.

Specifically, when a solvent evaporation method is preferably employed, a single crystal having the above size can be advantageously obtained by maintaining a bath at a constant temperature, circulating an inert gas such as an argon gas to control the evaporation rate of a solvent.

The FMA single crystal of the present invention has further characteristic features that it has an absorption edge in a region of light having a wavelength of not more than 450 nm, and exhibits non-linear optical activity. The term "absorption edge" refers to an edge value of an absorption band on a long wavelength side when a crystal is measured for an absorption spectrum with a spectrophotometer.

The non-linear optical activity is as large as $d_{33}=27$ pm/V.

The crystal structure of the FMA single crystal of the present invention comes under a space group of $I4_1cd$ and belongs to a tetragonal system. In addition, the FMA single crystal of the present invention has also a characteristic feature in that a phase matching method of type II can be applied thereto.

Due to the above-described characteristic features, the FMA single crystal of the present invention is particularly industrially excellent as a non-linear optical material. For example, being a bulky body having a size of which the largest side is at least 1 mm means having high non-linear optical activity. The FMA single crystal of the present invention is therefore suitable for a material as non-linear optical elements used in the field of optoelectronics, e.g., for a material as a light wavelength conversion element.

The FMA single crystal of the present invention generates, for example, all intense second harmonic wave (green light at 532 nm) under irradiation with an Nd:YAG laser (1064 nm). Further, since the FMA single crystal of the present invention has an absorption edge in a region of light having a wavelength of not more than 450 nm, i.e., is nearly transparent in a visible light region, it is useful as a material for an element in converting the wavelength of a semiconductor laser light. Furthermore, the FMA single crystal of the present invention is very useful as a material for manufacturing a light wavelength conversion element, an optical switch element and a variety of non-linear optical devices using these.

According to the present invention, therefore, there are also provided a light wavelength conversion element and an optical switch element both formed from the FMA single crystal of the present invention.

The present invention will be described further in detail hereinafter by reference to Examples. However, the present invention shall not be limited thereto.

EXAMPLE 1

(1) An eggplant type flask was charged with 30.0 g of 3-(2-furyl)methacrylic acid, 23.5 g of pyridine and 500 ml of benzene, and 17.5 g of thionyl chloride was gradually added dropwise thereto through a dropping funnel. After the addition, the resultant mixture was stirred at room temperature for a while, and then stirred under heat at 50° C. for 2 hours. The reaction mixture was washed with water, a diluted alkaline aqueous solution and then a diluted hydrochloric acid aqueous solution. A formed solid was recovered by filtration. A benzene layer was separated from the filtrate, and the remainder was dried over anhydrous sodium sulfate. A mixture of a solid obtained after removing the benzene layer and the solid recovered by filtration was recrystallized from a benzene/hexane mixed solvent to give 17.4 g of a colorless, fine-powder crystal of 3-(2-furyl)methacrylic acid anhydride. The yield thereof was 62%.

The instrumental analysis results of the above-obtained crystal were as follows.

mp.: 135° C.

Absorption spectrum (in ethanol): λ cutoff; 357 nm,
IR(cm$^{-1}$): 1,750 (C=O), 1,622 (CH=CH)
$^1$H-NMR (in CDCl$_3$, tetramethylsilane as a standard): δ=2.29 ppm (s,6H), 6.50–7.70 ppm (m,8H)

Mass: $m/e = 286(M+), 135$

Elemental analysis value $(C_{16}H_{14}O_5 = 286.27)$ Found (%) C, 67.28; H, 5.08 Calculated (%) C, 67.38, H, 4.93

(2) The above-synthesized fine-powder crystal of 3-(2-furyl)methacrylic acid anhydride was dissolved in acetone to obtain a saturated solution. A seed crystal of FMA was added to the saturated solution in a flask. Then, the flask was immersed in a water vessel set at 12° C., and the acetone was gradually evaporated under an argon stream to give a single crystal having a size of $35 \times 7 \times 4$ mm. This single crystal was stable in atmosphere.

Ultraviolet Visible Light Spectra of Single Crystal

The above-obtained single crystal was measured for visible light ultraviolet spectra to show that the absorption edge was at 400 nm.

Refractive Index of Single Crystal

The above-obtained single crystal was measured for refractive indices by the Brewster angle method to give $n_o = 1.594$ and $n_e = 1.789$ for light having wavelength of 1,064 nm and $n_o = 1.684$ and $n_e = 1.923$ for light having a wavelength of 532 nm.

Performance Index of Single Crystal

The above-obtained single crystal was measured for second harmonic generation activity by a Maker fringe method to give $d_{33} = 27$ pm/v in comparison with a rock crystal.

Phase Matching Method Using Single Crystal

The above-obtained single crystal was fixed on a goniohead and irradiated with Nd:YAG laser light (wavelength; 1064 nm). As a result, non-colinear type II phase matching was achieved, and a green, second harmonic wave was obtained in the direction at an angle of 10 degrees with regard to a basic wave.

X-ray Analysis of Crystal Structure

A single crystal formed in acetone in the same manner as in the formation of the above single crystal was subjected to X-ray analysis to show that the analyzed FMA single crystal came under the space group of $14_1cd$ and belonged to a tetragonal system $(Z=8)$. The unit cell thereof had a size of $a = b = 1.6103$ nm and $c = 1.0679$ nm. The FMA single crystal used in the above X-ray analysis was a fine single crystal having a size of which the largest side was not more than 1 mm long.

COMPARATIVE EXAMPLE 1

A fine-powder crystal of 2-ethyl-3-(2-furyl)acrylic acid anhydride was prepared from 2-ethyl-3-(2-furyl)acrylic acid in the same manner as in Example 1. Then, the fine-powder crystal was dissolved in acetone and the acetone was evaporated by circulating an argon gas in the same manner as in Example 1 to form a single crystal of 2-ethyl-3-(2-furyl)acrylic acid anhydride having a size of $5 \times 2 \times 1.5$ mm. The single crystal was fixed on a goniohead and irradiated with Nd:YAG laser light (wavelength; 1064 nm). The output of the second harmonic wave in green was very low.

What is claimed is:

1. A single crystal of 3-(2-furyl)methacrylic acid anhydride,
   (a) which has an absorption edge in a region of light having a wavelength of not more than 450 nm
   (b) which exhibits non-linear optical activity,
   (c) which has a single crystal structure having a size of which the largest side is at least 1 mm long, and
   (d) which consists of 3-(2-furyl)methacrylic acid anhydride of the following formula (I)

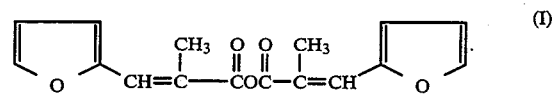

2. A single crystal according to claim 1, having a size of which the smallest side is at least 0.5 mm long and having the form of a prism or a pyramid.

3. A single crystal according to claim 2 wherein the length of the longest side of said crystal is at least 1 millimeter.

4. A single crystal according to claim 1 wherein the length of the longest side of said crystal is at least 1 millimeter.

5. A single crystal according to claim 1 in the form of a prism or a pyramid in which the shortest side is at least 1 millimeter long and the longest side is at least 2 millimeters long.

6. A single crystal according to claim 1 having a Vickers hardness of at least 20.

7. A single crystal according to claim 1 having an absorption edge at 400 nm.

* * * * *